US00PP33624P2

(12) United States Plant Patent
Pineau

(10) Patent No.: US PP33,624 P2
(45) Date of Patent: Nov. 9, 2021

(54) ***COTINUS* PLANT NAMED 'MINCOFLA20'**

(50) Latin Name: *Cotinus coggygria*
Varietal Denomination: MINCOFLA20

(71) Applicant: Hortival Diffusion SAS, Beaufort en Valee (FR)

(72) Inventor: Patrick Pineau, Saint Mathurin sur Loire (FR)

(73) Assignee: Hortival Diffusion SAS

( * ) Notice: Subject to any disclaimer, the term of this patent is extended or adjusted under 35 U.S.C. 154(b) by 0 days.

(21) Appl. No.: 17/038,873

(22) Filed: Sep. 30, 2020

(51) Int. Cl.
*A01H 5/02* (2018.01)
*A01H 6/00* (2018.01)

(52) U.S. Cl.
USPC ..... Plt./226
CPC ..... *A01H 6/00* (2018.05)

(58) Field of Classification Search
USPC ..... Plt./226
CPC ..... A01H 6/00
See application file for complete search history.

(56) References Cited

PUBLICATIONS

*Cotinus coggygria* Flamissio, Polish Nurserymen Association, https://zszp.pl/en/plants/plant-novelties-competition-zszp/plant-novelties-competition-2019/cotinus-coggygria-flamissio/ published Jul. 24, 2019.*
UPOV hit on *Cotinus* plant named, 'Mincofla20', QZ PBR 20191492, filed Jun. 20, 2019.*
UPOV hit on *Cotinus* plant named 'MINCOFLA20', QZ PBR 20191492, published Jun. 21, 2019.*

* cited by examiner

*Primary Examiner* — Anne Marie Grunberg
(74) *Attorney, Agent, or Firm* — Cassandra Bright

(57) ABSTRACT

A new and distinct cultivar of *Cotinus* plant named 'MINCOFLA20' is disclosed, characterized by green and greyed-purple foliage color in Spring, green foliage in Summer, and bright orange foliage in Autumn. Plants are well-branched with medium vigor. Inflorescences are distinctively light red. The new variety is a *Cotinus*, normally produced as an outdoor garden or container plant.

4 Drawing Sheets

Latin name of the genus and species: *Cotinus coggygria*.
Variety denomination: 'MINCOFLA20'.

BACKGROUND OF THE INVENTION

The new *Cotinus* cultivar is a product of a planned breeding program conducted by the inventor in La Menitre, France. The objective of the breeding program was to produce new *Cotinus coggygria* varieties having good branching habits and interesting colored foliage. The crossing resulting in this new variety was made during 2008.

The seed parent is *Cotinus coggygria* 'Young Lady', unpatented, the pollen parent is an unpatented, proprietary seedling of *Cotinus coggygria* referred to as 'n11159'. The new variety was identified as a potentially interesting selection during July of 2012. Selection was made at a research nursery in La Menitre, France.

Asexual reproduction of the new cultivar 'MINCOFLA20' was first performed July of 2012 at a commercial nursery in La Menitre, France. Vegetative stem cuttings were used. Subsequent propagation has shown that the unique features of this cultivar are stable and reproduced true to type in successive generations. Date of first sale was Oct. 1, 2019, occurring in France. This sale was made directly by the inventor or one who obtained the claimed invention directly or indirectly from the inventor. This sale and all public disclosures made between Oct. 1, 2019 and the filing of this application fall within the exception allowed under 102(b)(1).

SUMMARY OF THE INVENTION

The cultivar 'MINCOFLA20' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'MINCOFLA20' These characteristics in combination distinguish 'MINCOFLA20' as a new and distinct *Cotinus* cultivar:

1. Plants have a well-branched growth habit and medium vigor.
2. Green and greyed-purple foliage color in Spring, green foliage in Summer, bright orange foliage in Autumn.
3. Light red inflorescences.

PARENT COMPARISON

Plants of the new cultivar 'MINCOFLA20' are similar to plants of the seed parent variety in most horticultural characteristics, however, plants of the new cultivar 'MINCOFLA20' differ in the following;

1. Plants of the new variety are larger than plants of the seed parent.
2. New foliage of 'MINCOFLA20' is green and greyed-purple; new foliage of 'Young Lady' is green.
3. Fall foliage of the new variety is bright orange; Fall foliage of the seed parent is green.

4. The inflorescences of the new variety are larger than inflorescences of the seed parent.

Plants of the new cultivar 'MINCOFLA20' are similar to plants of the pollen parent variety in most horticultural characteristics, however, plants of the new cultivar 'MINCOFLA20' differ in the following;

1. Fall foliage of the new variety is bright orange; Fall foliage of the pollen parent is green.

COMMERCIAL COMPARISON

Plants of the new cultivar 'MINCOFLA20' can be compared to the variety *Cotinus* 'NCC01', U.S. Plant Pat. No. 30,216. These varieties are similar in most horticultural characteristics however, 'MINCOFLA20' differs in the following:

1. The new variety has bright orange Fall foliage, 'NCC01' has somewhat red-orange Fall foliage.
2. Inflorescences of the new variety are light red, inflorescences of 'NCC01' are maroon.
3. Spring/Summer foliage of the new variety is Green/greyed-purple, Spring/Summer foliage of 'NCC01' is dark purple.

BRIEF DESCRIPTION OF THE PHOTOGRAPHS

The accompanying photograph in FIG. 1 illustrates in full color a typical blooming plant of 'MINCOFLA20' grown outdoors, in a 3 gallon container at approximately 2.5 years old.

Figure 1:
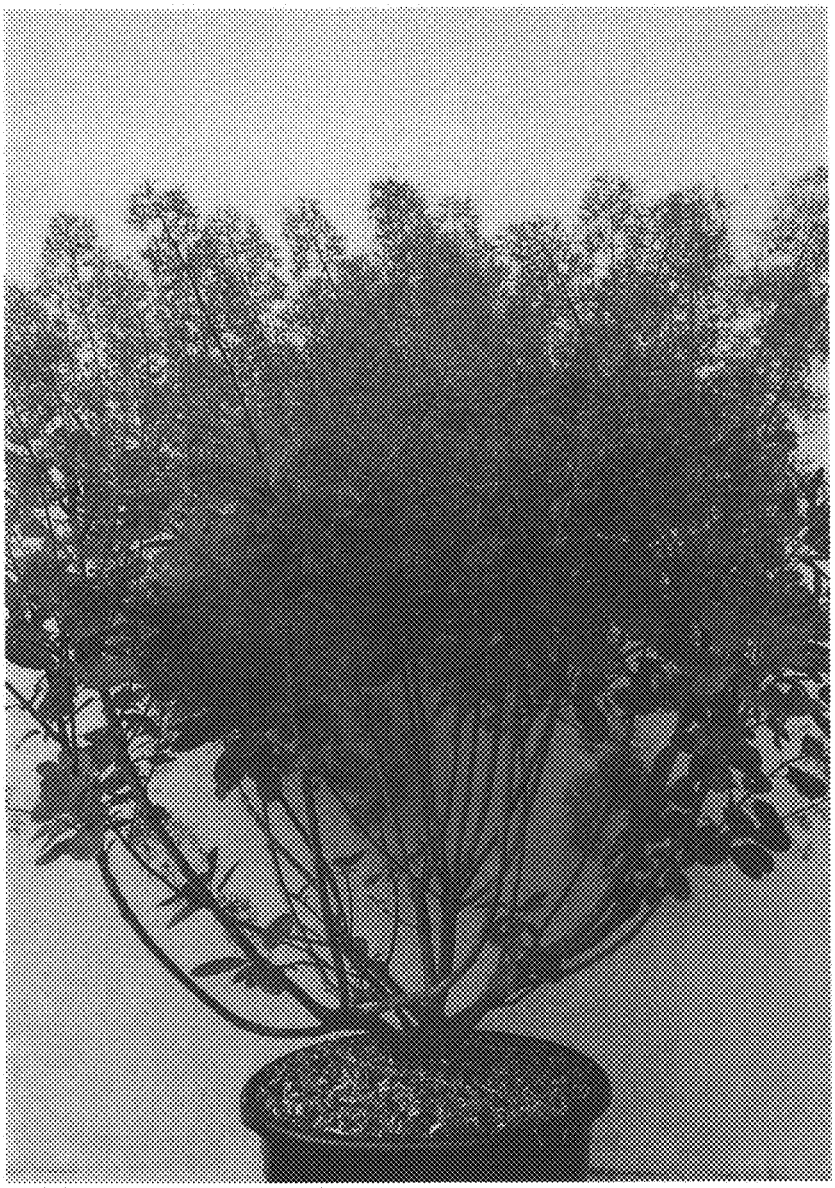
Figure 2:
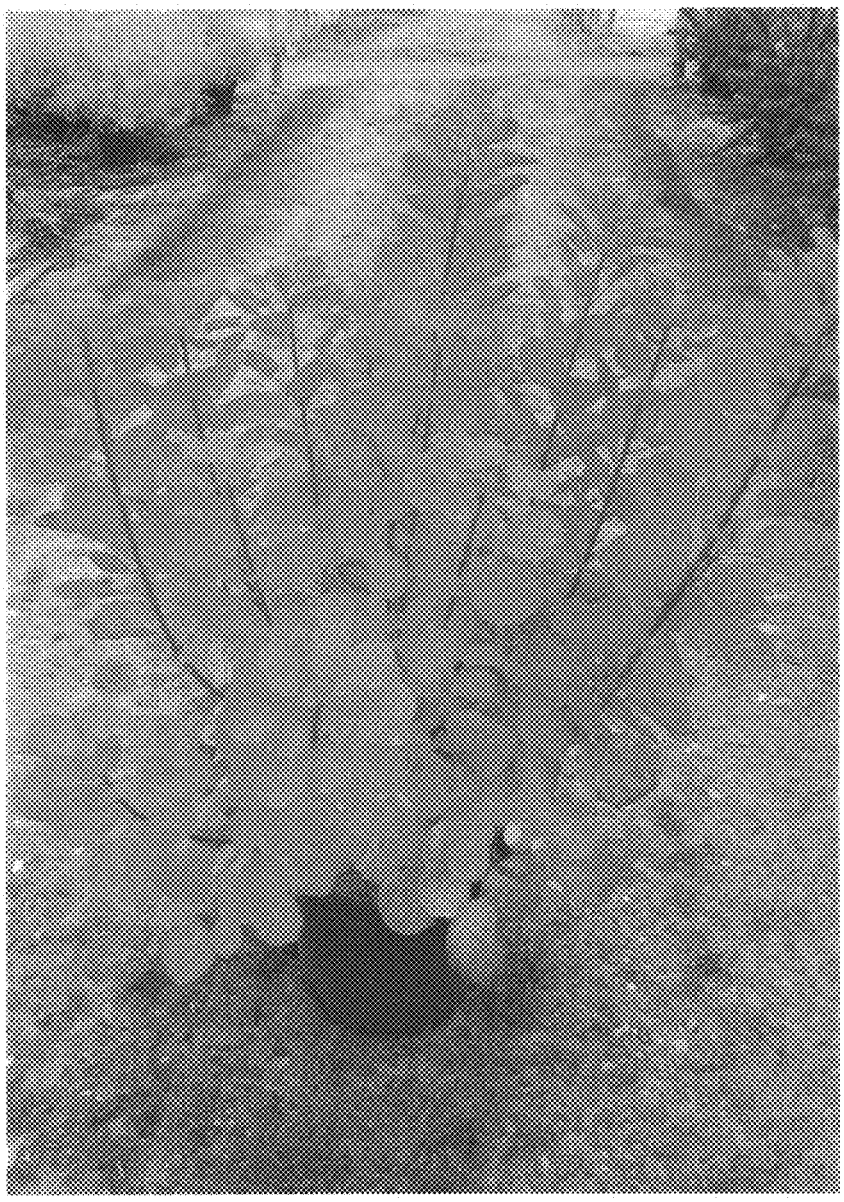
FIG. 2 illustrates Fall foliage color.
Figure 3:
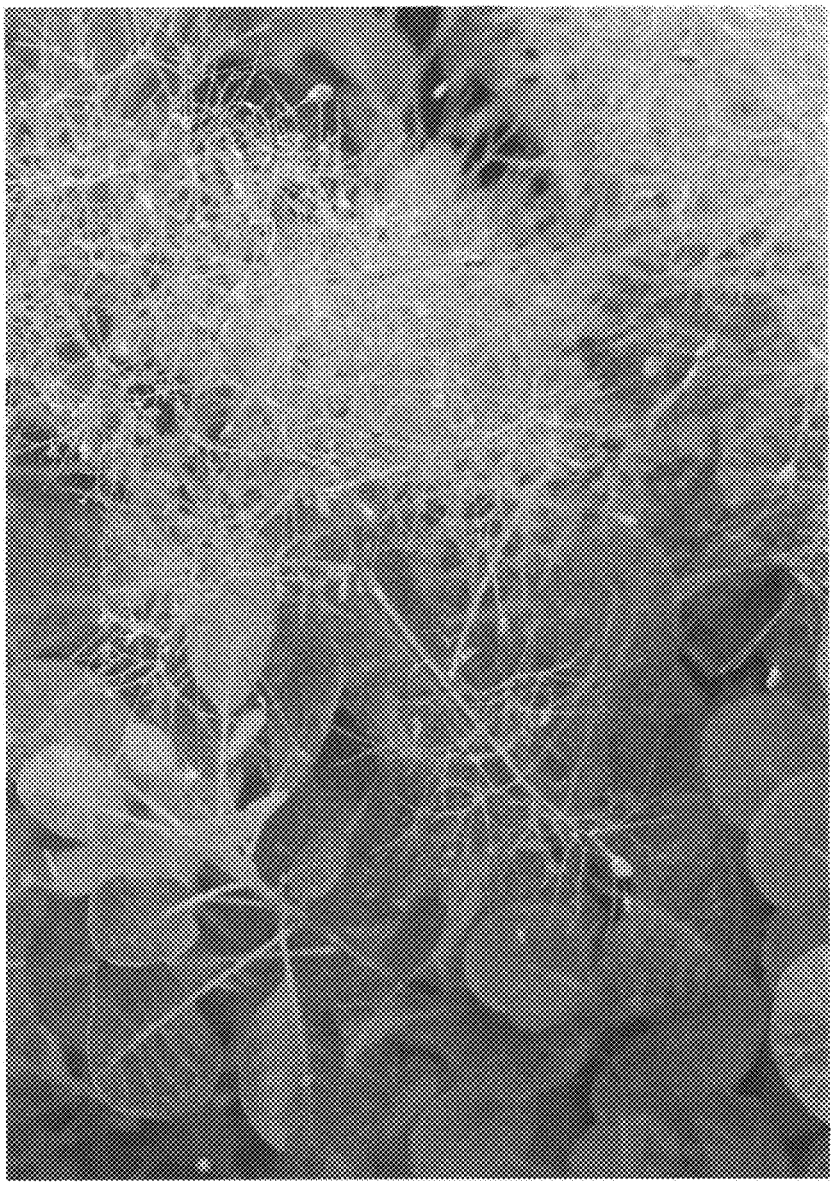
FIG. 3 illustrates in full color a typical inflorescence of 'MINCOFLA20'.
Figure 4:
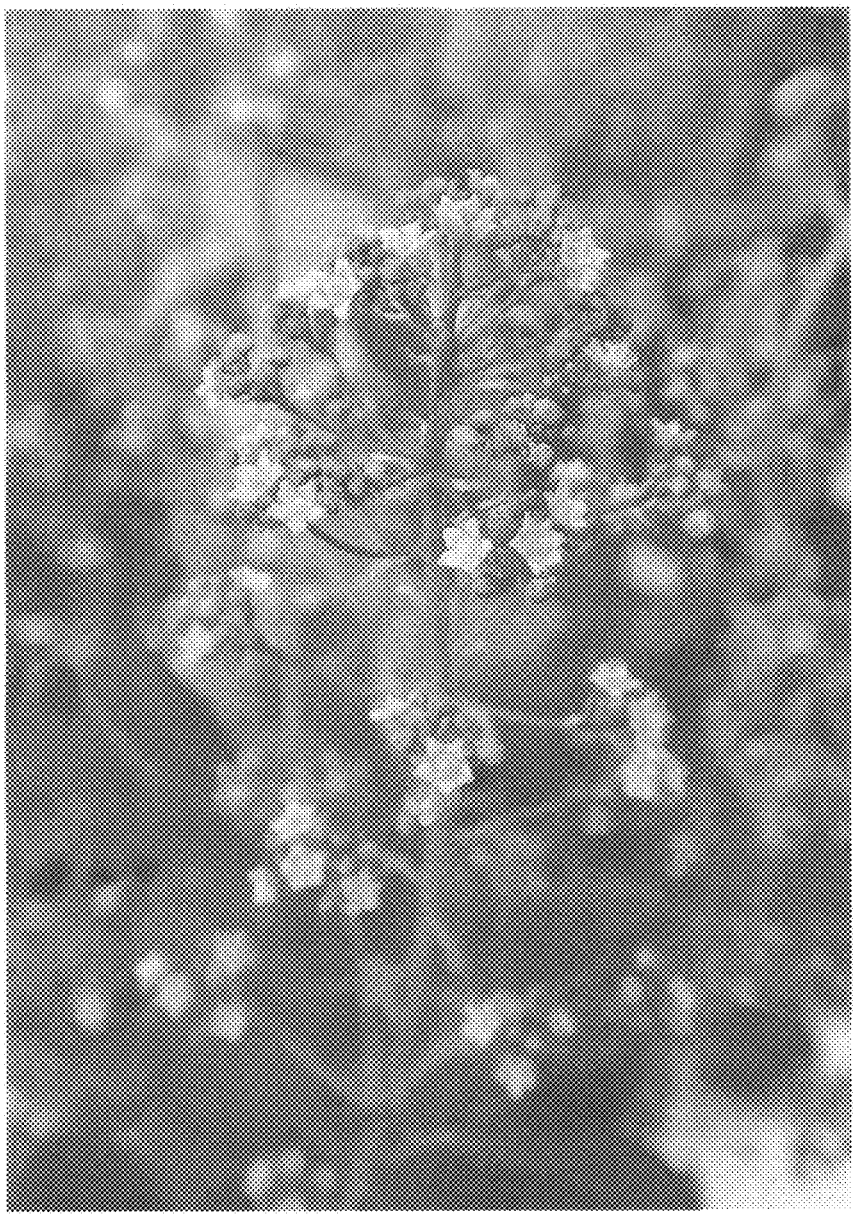
FIG. 4 shows individual flowers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, $6^{th}$ edition, except where general terms of ordinary dictionary significance are used. The following observations and measurements describe 'MINCOFLA20' plants grown in a polyhouse in Grand Haven, Mich. Measurements were taken during May. The plants were about 2.5 years old, planted in the ground in a test field. The growing temperature ranged from approximately 18° C. to 27° C. during the day and 5° C. to 10° C. at night. Measurements and numerical values represent averages of typical plant types.

Botanical classification: *Cotinus coggygria* 'MINCOFLA20'.

PROPAGATION

Time to initiate roots: About 6 weeks at approximately 18° C. to 27° C.

Root description: Dense. Tan/white in color, not effectively measured with a color chart.

Time to produce a rooted young plant: About 12 days at approximately 18° C. to 27° C.

PLANT

Plant type: Perennial shrub.

Age of plant described: Approximately 2.5 years old.

Growth habit: Upright, outwardly spreading.

Overall plant shape: Globular upright.

Height: 180 cm.

Plant spread: 140 cm.

Plant vigor: Moderate.

Branching characteristics: Upright and compact. Basal and lateral branching. Pinching not required.

Length of primary lateral branches: Average range 120 to 150 cm.

Diameter of lateral branches: 3 mm.

Quantity of lateral branches: Average 13.

Stem:

*Stem shape.*—Round.

*Stem strength.*—Moderate.

*Color.*—Stem: Near RHS Greyed-Orange 177A mixed with Greyed-Red 181A.

*Texture.*—Glabrous.

*Angle of attachment.*—Acute, 0 to 20 degrees from center of plant.

Internode length: 1.5 cm on average.

FOLIAGE

Leaf:

*Arrangement.*—Opposite to sub-opposite, single.

*Leaves per branch.*—Average range 20 to 60, depending upon length of branch.

*Leaf shape.*—Obovate.

*Length.*—3.75 cm.

*Width.*—2.75 cm.

*Apex.*—Acute.

*Base.*—Cuneate.

*Margin.*—Entire.

*Texture of top surface.*—Glabrous with some vein ridges.

*Texture of bottom surface.*—Leathery with some vein ridges.

*Color.*—Spring foliage upper side: Near RHS Greyed-Purple 183C mixed with Green 138A. Green color more prominent with maturity. Spring foliage under side: Near RHS Green 138B. Summer foliage upper side: Near RHS Green NN137B. Summer foliage under side: Near RHS Yellow-Green 147B. Fall foliage upper side: Initial Fall color near Greyed-Orange 163B, turning Red 41A. Fall foliage under side: Initial Fall color near Greyed-Orange 163B, turning Red 41A.

*Venation.*—Pattern: Palmate. Color: Spring and Summer color same as leaf blade. Fall Color upper side: Near RHS Red 41C. Fall Color under side: Near RHS Greyed-Orange 163C.

*Petiole.*—Average Length: 15 mm. Diameter: 1 mm. Petiole color upper side: Near RHS Greyed-Orange 173B. Petiole color lower side: Near RHS Greyed- Orange 160A. Petiole Texture upper side: Smooth. Petiole Texture lower side: Smooth.

FLOWER

Natural flowering season: May to June.
Inflorescence:
*Type*.—Panicle.
*Length/height*.—10 cm.
*Width*.—10 cm.
*Flowers per inflorescence*.—Average range 100 to 200.
Flower:
*Type*.—Single rotate.
*Diameter*.—4 mm.
*Height*.—4 mm.
*Aspect*.—Upwardly and outwardly facing.
*Persistent or self-cleaning*.—Self-cleaning.
*Fragrance*.—None detected.
Petal:
*Number*.—5.
*Arrangement*.—Single whorl.
*Fused*.—Not fused.
*Base*.—Rounded.
*Shape*.—Ovate.
*Margin*.—Entire.
*Apex*.—Acute.
*Length*.—1 mm.
*Width*.—1 mm.
*Color*.—When opening, upper side: Yellow-Green 154C. Fully opened, upper side: Yellow-Green 154C.
*Petaloids*.—Absent.
Flower bud:
*Shape*.—Oblong.
*Diameter*.—1 mm.
*Height*.—1 mm.
*Color*.—Near RHS Green 143C.
Calyx:
*Shape*.—Cup-shaped.
*Length*.—1 mm.
*Diameter*.—1 mm.
*Color*.—Yellow-Green 144C.
Peduncles:
*Length*.—7 mm.
*Diameter*.—1 mm.
*Angle*.—About 45° to the lateral branch.
*Strength*.—Moderate.
*Texture*.—Glabrous.
*Color*.—RHS Yellow-Green 144C flushed Greyed-Purple 185A.
Pedicels:
*Length*.—5 mm.
*Diameter*.—1 mm.
*Angle*.—About 45° to the lateral branch.
*Strength*.—Moderate.
*Texture*.—Glabrous.
*Color*.—RHS Greyed-Purple 185C.

REPRODUCTIVE ORGANS

Stamens:
*Number*.—5.
*Filament length*.—1 mm.
*Filament color*.—Near RHS Yellow-Green 144B.
*Anther shape*.—Kidney shaped.
*Length*.—Less than 1 mm.
*Color*.—Near RHS Yellow-Orange 15A.
*Pollen color*.—Near RHS Yellow-Orange 15A.
*Pollen amount*.—Scant.
Pistil:
*Number*.—1.
*Length*.—Less than 1 mm.
*Style*.—Length: Less than 1 mm. Color: Near RHS Yellow-Green 144B.
*Stigma*.—Shape: Club-shaped. Color: Near RHS Yellow-Green 144B.
*Ovary color*.—Near RHS Yellow-Green 144B.

OTHER CHARACTERISTICS

Seeds and fruits: Not observed to date.
Disease/pest resistance: Neither resistance nor susceptibility to normal diseases and pests of *Cotinus coggygria* have been observed.
Garden performance: Good tolerance, performs well in humid conditions.
Temperature tolerance: −18° C. to 35° C.

What is claimed is:

1. A new and distinct cultivar of *Cotinus* plant named 'MINCOFLA20' as herein illustrated and described.

* * * * *